US008773758B2

(12) United States Patent
Nakayama et al.

(10) Patent No.: US 8,773,758 B2
(45) Date of Patent: Jul. 8, 2014

(54) MICROSCOPE APPARATUS WITH AN IMAGING SYSTEM INCLUDING AN ASTIGMATIC DIFFERENCE CHANGING DEVICE

(71) Applicant: Nikon Corporation, Tokyo (JP)

(72) Inventors: Hiroaki Nakayama, Kawasaki (JP); Yumiko Ouchi, Yokohama (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 13/687,347

(22) Filed: Nov. 28, 2012

(65) Prior Publication Data

US 2013/0088776 A1   Apr. 11, 2013

Related U.S. Application Data

(63) Continuation of application No. PCT/JP2011/062808, filed on Jun. 3, 2011.

(30) Foreign Application Priority Data

Jun. 3, 2010  (JP) ................................. 2010-127906

(51) Int. Cl.
*G02B 21/02* (2006.01)
(52) U.S. Cl.
USPC .......................................... 359/381; 359/384
(58) Field of Classification Search
USPC .......................................... 359/381, 384, 385
See application file for complete search history.

(56) References Cited

U.S. PATENT DOCUMENTS

| 5,191,474 | A | | 3/1993 | Suzuki et al. |
| 5,880,465 | A | * | 3/1999 | Boettner et al. ............... 250/234 |
| 6,388,788 | B1 | * | 5/2002 | Harris et al. ................ 359/196.1 |
| 7,221,503 | B2 | * | 5/2007 | Eberhardt et al. ............ 359/385 |
| 7,733,564 | B2 | * | 6/2010 | Wolleschensky et al. ..... 359/385 |
| 7,911,670 | B2 | * | 3/2011 | Bec et al. .................... 359/221.2 |

(Continued)

FOREIGN PATENT DOCUMENTS

| EP | 1 840 623 A2 | 10/2007 |
| JP | A-03-210516 | 9/1991 |

(Continued)

OTHER PUBLICATIONS

Donald K. Cohen et al., "Automatic focus control: the astigmatic lens approach", Applied Optics, vol. 23, No. 4, Feb. 15, 1984, pp. 565-570.*

(Continued)

*Primary Examiner* — Frank Font
(74) *Attorney, Agent, or Firm* — Oliff PLC (57) ABSTRACT

There is provided a microscope apparatus including: a plurality of objective lenses having different magnifications; an imaging system that receives light, which is generated from a sample and emitted from the objective lens when excitation light is emitted to a sample including a fluorescent material that is activated when irradiated with activation light having a predetermined wavelength and fluoresces to be inactivated when irradiated with excitation light having a different wavelength from the activation light in the activation state and that images the light in a state where an astigmatic difference is given to the image of the sample; and an imaging device that captures the image of the sample from the imaging system. The imaging system includes an astigmatic difference changing device that changes the astigmatic difference according to the depth of focus of the objective lens.

13 Claims, 10 Drawing Sheets

(56) References Cited

U.S. PATENT DOCUMENTS

| | | | |
|---|---|---|---|
| 8,270,088 B2* | 9/2012 | Yokoi | 359/637 |
| 8,351,115 B2* | 1/2013 | Isozaki et al. | 359/363 |
| 2007/0081236 A1* | 4/2007 | Tearney et al. | 359/390 |
| 2007/0146873 A1* | 6/2007 | Ortyn et al. | 359/386 |
| 2007/0236687 A1 | 10/2007 | Mikuriya et al. | |
| 2008/0032414 A1 | 2/2008 | Zhuang et al. | |
| 2008/0182336 A1 | 7/2008 | Zhuang et al. | |
| 2010/0278400 A1* | 11/2010 | Piestun et al. | 382/128 |
| 2011/0006231 A1* | 1/2011 | Betzig et al. | 250/578.1 |
| 2011/0178409 A1* | 7/2011 | Harris et al. | 600/476 |
| 2012/0300055 A1* | 11/2012 | Salisbury et al. | 348/79 |

FOREIGN PATENT DOCUMENTS

| | | |
|---|---|---|
| JP | A-2005-243904 | 9/2005 |
| JP | A-2007-271978 | 10/2007 |
| JP | A-2008-203813 | 9/2008 |
| JP | A-2010-102332 | 5/2010 |

OTHER PUBLICATIONS

Bo Huang et al. "Three-Dimensional Super-Resolution Imaging by Stochastic Optical Reconstruction Microscopy" 2008, *Science* vol. 319, pp. 810-813.

Aug. 30, 2011 International Search Report issued in International Patent Application No. PCT/JP2011/062808 (with translation).

Aug. 30, 2011 Written Opinion issued in International Patent Application No. PCT/JP2011/062808 (with translation).

Aug. 27, 2013 Office Action issued in Japanese Patent Application No. 2012-518467 (with translation).

\* cited by examiner

MICROSCOPE APPARATUS WITH AN IMAGING SYSTEM INCLUDING AN ASTIGMATIC DIFFERENCE CHANGING DEVICE

CROSS-REFERENCE TO RELATED APPLICATION

This is a Continuation Application of International Application No. PCT/JP2011/062808, filed Jun. 3, 2011, which claims priority to Japanese Patent Application No. 2010-127906 filed on Jun. 3, 2010. The contents of the aforementioned applications are incorporated herein by reference.

BACKGROUND

1. Field of the Invention

The present invention relates to a microscope apparatus.

2. Description of Related Art

Regarding a super-resolution microscope in the related art, STORM (Stochastic Optical Reconstruction Microscopy) is known (for example, refer to United States Patent Application, Publication No. 2008/0032414 and United States Patent Application, Publication No. 2008/0182336). In this microscope, a fluorescent material or a sample having a fluorescent material adhering thereto is used as an observed sample. This fluorescent material has a characteristic of being activated when irradiated with activation light having a predetermined wavelength and fluorescing to be inactivated when irradiated with excitation light having a different wavelength from the activation light later. A fluorescent material is activated with low density by irradiating an observed sample with weak activation light. By emitting excitation light later in order to make only the activated fluorescent material emit light, a fluorescent image is acquired. In the fluorescent image acquired in this manner, images of the fluorescent material that emits light with low density are separated individually. Accordingly, it is possible to obtain the position of the center of gravity of each image. By repeating such a step of obtaining the position of the fluorescent material multiple times, for example, hundreds of times to tens of thousands of times or more to create one image in which all images of the fluorescent material are disposed at their positions, it is possible to acquire a high-resolution observation image.

In addition, as a super-resolution microscope apparatus, a STORM based on a three-dimensional method capable of improving not only the resolution within the sample surface (XY plane) but also the resolution in the thickness direction (Z direction) of the sample is known (for example, refer to Bo Huang, et. al. Science 319, 810-813 (2008)). In such a STORM based on the three-dimensional method, the image of a fluorescent material can be made to have an elliptical shape by giving a predetermined astigmatic difference to the image of the sample by inserting a cylindrical lens in the imaging optical system, and the coordinate in the Z direction can be obtained from the ellipticity.

SUMMARY

In the STORM based on the three-dimensional method, however, if the magnification or the numerical aperture of an objective lens is changed according to the image acquisition conditions of a sample, the coordinate of the Z position may not be measured correctly.

An object of aspects of the present invention is to provide a microscope apparatus capable of obtaining a high-resolution observed image.

According to an aspect of the present invention, there is provided a microscope apparatus including: a plurality of objective lenses having different magnifications; an imaging system that receives light, which is emitted from a sample including a fluorescent material, through the objective lens and that supplies an image of the sample to which an astigmatic difference is given; and an imaging device that captures the image of the sample from the imaging system. The imaging system includes an astigmatic difference changing device that changes the astigmatic difference according to a depth of focus of the objective lens.

According to the aspects of the present invention, the astigmatic difference can be optimized according to the image acquisition conditions of a sample.

DESCRIPTION OF EMBODIMENTS

Hereinafter, the configuration according to an embodiment of a microscope apparatus of the present invention will be described with reference to the drawings. In addition, the present embodiment is intended to explain the summary of the invention in detail so that it can be better understood, and does not limit the present invention unless otherwise specified. In addition, in the drawings used in the following explanation, main sections may be shown in an enlarged manner for the sake of convenience so that the features can be easily understood. Accordingly, the scale or the like of each requested element is not necessarily the same as the actual scale.

(First Embodiment)

Figure 1:
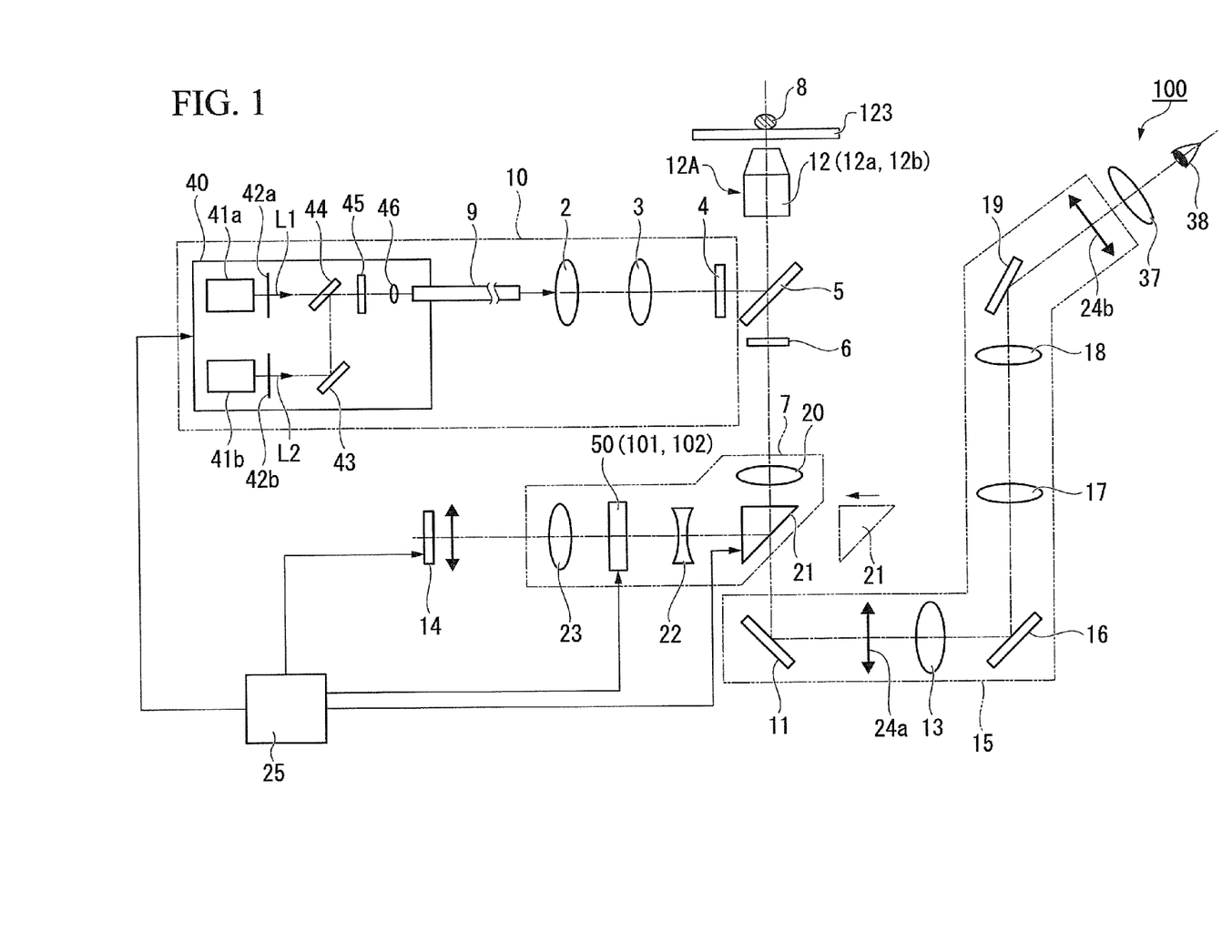
FIG. 1 is a view showing the schematic configuration of a microscope apparatus according to a first embodiment.

FIG. 1 is a view showing the schematic configuration of the microscope apparatus according to the present embodiment. As shown in FIG. 1, a microscope apparatus 100 includes an illumination system 10, a stage 123 on which a sample 8 is placed, an objective lens unit 12A disposed opposite the sample 8 on the stage 123, an imaging optical system (imaging system) 7, an imaging device 14 that captures an image of the sample 8 imaged by the imaging optical system 7, a relay optical system 15, and a control unit 25 that performs overall control of the microscope apparatus 100.

The microscope apparatus 100 according to the present embodiment uses STORM (Stochastic Optical Reconstruction Microscopy) corresponding to a two-dimensional method or a three-dimensional method. In the microscope apparatus 100, a sample labeled with a fluorescent material is used. This fluorescent material is activated when irradiated with activation light having a predetermined wavelength. In addition, the fluorescent material fluoresces to be inactivated when irradiated with excitation light having a different wavelength from the activation light in the activated state. In addition, an operation to observe the fluorescence discretely distributed is repeated by making only some fluorescent materials in a sample emit light using the excitation light and the activation light. A sample image can be formed using a number of fluorescent images acquired as a result. In addition, the fluorescent material may contain organic compounds, such as Cy5 and Alexa647. In addition, the fluorescent material may contain a fluorescent protein, such as PA-GFP.

The illumination system 10 includes a laser unit 40, a fiber 9, lenses 2 and 3, and an excitation filter 4. The laser unit 40 has a first laser light source 41 a and a second laser light source 41b. The first laser light source 41a emits activation light L1 for activating a fluorescent material given to a sample. The first laser light source 41 a emits the activation light L1 having a wavelength suitable for the fluorescent material included in the sample. As examples of the first laser light source 41 a, it is possible to use a green laser (wavelength of 532 nm), a red laser (wavelengths of 633 nm and 657 nm), a purple laser (wavelength of 405 nm), a blue laser (wavelength of 457 nm), and the like depending on the type of fluorescent material.

The second laser light source 41b emits excitation light L2 for making a fluorescent material given to a sample emit light. The second laser light source 41b emits the excitation light L2 having a wavelength suitable for the fluorescent material included in the sample. As examples of the second laser light source 41b, it is possible to use a green laser (wavelength of532 nm), a red laser (wavelengths of 633 nm and 657 nm), a purple laser (wavelength of 405 nm), a blue laser (wavelength of 457 nm), and the like depending on the type of fluorescent material. The laser unit 40 has shutters 42a and 42b that are respectively disposed before the laser light sources 41a and 41b, a mirror 43 that reflects the light L2 from the laser light source 41b, a dichroic mirror 44 that makes the light L1 from the laser light source 41a be transmitted therethrough and the light L2 from the laser light source 41b be reflected therefrom, an acousto-optical element 45 that adjusts the intensity of incident laser light, and a coupler 46 for condensing laser light on the incidence end of the fiber 9. In addition, the control unit 25 is connected to the laser unit 40. The control unit 25 controls the opening and closing of the shutters 42a and 42b to perform irradiation switching of the activation light L1 and the excitation light L2. In addition, at the same time, the control unit 25 controls the acousto-optical element 45 to adjust the intensity of laser light incident on the fiber.

A dichroic mirror 5 is disposed on the optical path between the illumination system 10 and the objective lens unit 12A. The objective lens unit 12A includes a low-magnification objective lens 12a having a small depth of focus and a high-magnification objective lens 12b having a large depth of focus. Hereinafter, for convenience of explanation, the low-magnification objective lens 12a and the high-magnification objective lens 12b may be called collectively an objective lens 12. Illumination light from the illumination system 10 is condensed on the pupil plane of the objective lens 12 after being reflected by the dichroic mirror 5. Accordingly, the illumination light emitted from the objective lens 12 illuminates the sample 8.

As described above, the control unit 25 controls the sample 8 to be irradiated with the activation light L1 and the excitation light L2 from the laser light sources 41a and 41b. Light beams emitted from the sample 8 are incident on the objective lens 12 and are emitted as parallel light beams. The light is incident on the imaging optical system 7 after being transmitted through the dichroic mirror 5 and a barrier filter 6. The imaging optical system 7 includes an imaging lens 20, a prism 21, lenses 22 and 23 that configure an afocal optical system, and a cylindrical lens unit (astigmatic difference changing device) 50 provided between the lenses 22 and 23.

The control unit 25 is connected to the prism 21. In addition, a reciprocating mechanism (not shown) is provided in the prism 21, so that the prism 21 can move in and out with respect to the optical path. That is, when the prism 21 is inserted into the optical path, the prism 21 reflects light from the objective lens 12 to guide it to the imaging device 14.

The relay optical system 15 is configured by disposing a mirror 11, a lens 13, a mirror 16, lenses 17 and 18, and a mirror 19 behind the imaging lens 20. Light from the sample 8 is relayed by the relay optical system 15 when the prism 21 retreats from the optical path, and is observed by an observer (observing eye) 38 as an image of the sample 8 through an eyepiece 37.

Specifically, the light from the imaging lens 20 forms a primary image 24a after being reflected by the mirror 11. In addition, the light from the primary image 24a passes through the lens 13, is reflected by the mirror 16, passes through the lenses 17 and 18, and is reflected by the mirror 19. As a result, a secondary image 24b is formed. An observer 38 can visually observe the secondary image 24b through the eyepiece 37. In addition, the relay optical system 15 is used at the time of initial setting in which the observer 38 sets an image acquisition region in the sample 8, for example.

The microscope apparatus 100 according to the present embodiment can acquire the three-dimensional information of the sample 8 by giving an astigmatic difference, which will be described later, to the image of the sample 8 using the imaging optical system 7 and capturing the image of the sample 8 using the imaging device 14. The imaging device 14 is formed by an imaging device, such as a CCD camera, for example. The control unit 25 is connected to the imaging device 14.

Figure 2:
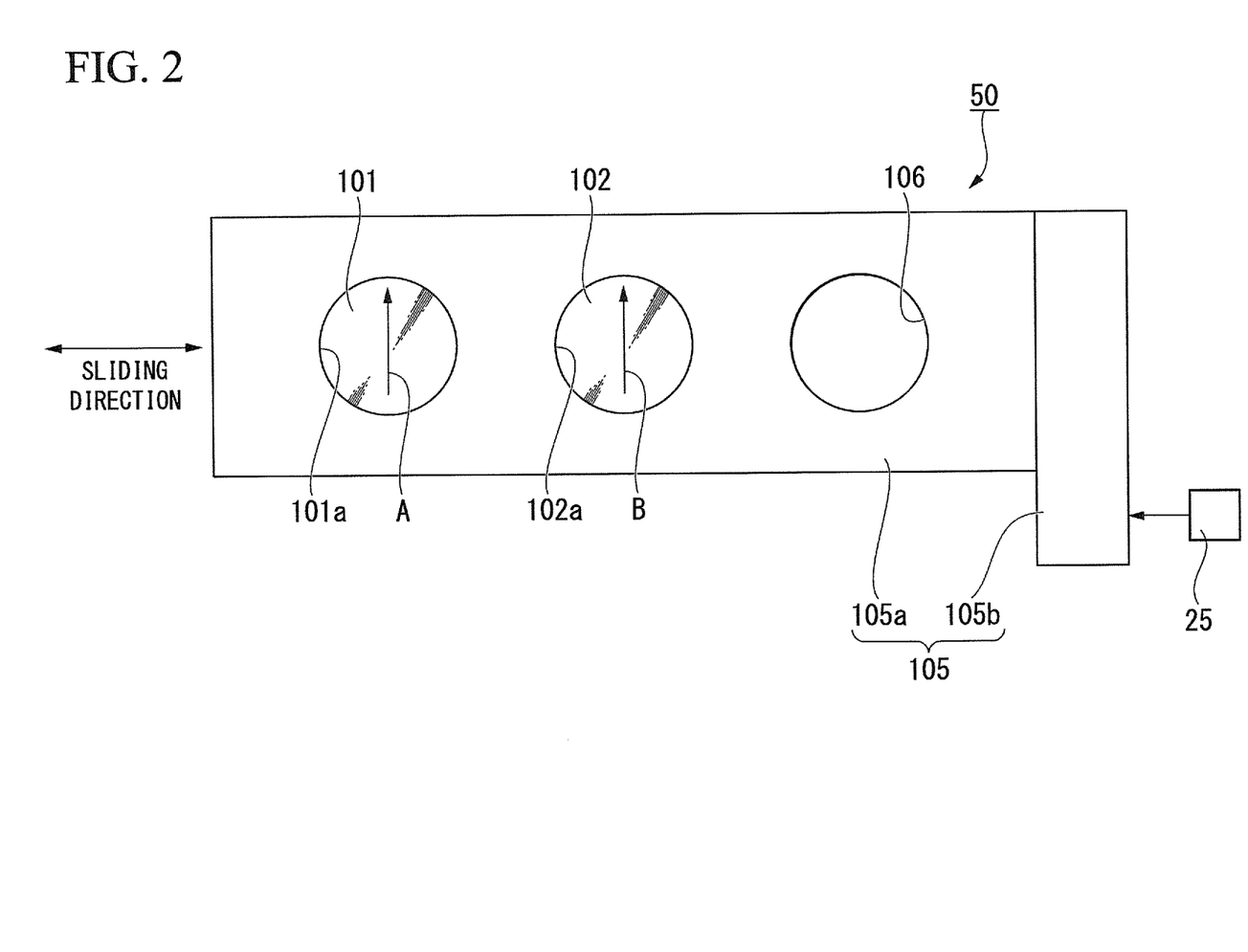
FIG. 2 is a view showing the configuration of a cylindrical lens unit according to the present embodiment.

In the present embodiment, in order to give an astigmatic difference to the image of the sample 8 using the imaging optical system 7, the imaging optical system 7 includes a cylindrical lens unit 50 shown in FIG. 2 between the lenses 22 and 23. The control unit 25 is connected to the cylindrical lens unit 50. As shown in FIG. 2, the cylindrical lens unit 50 includes cylindrical lenses 101 and 102 and a slider section (reciprocating section) 105 that moves the cylindrical lenses 101 and 102 back and forth between the lenses 22 and 23. The slider section 105 includes a sliding plate 105a that holds the cylindrical lenses 101 and 102 slidably between the lenses 22 and 23 and a driving section 105b that slides the sliding plate 105a. The control unit 25 is connected to the driving section 105b.

Holding sections 101a and 102a of the cylindrical lenses 101 and 102 and an opening section 106 are provided in the sliding plate 105a. The holding sections 101a and 102a and the opening section 106 are disposed along the sliding direction (horizontal direction) of the sliding plate 105a. The opening section 106 is set to have a size allowing light transmitted through the lens 22 to pass therethrough without blocking the light. The cylindrical lenses 101 and 102 are held on the sliding plate 105a when fitted in the holding sections 101a and 102a. In addition, the cylindrical lenses 101 and 102 have different focal lengths. Specifically, the focal length of the cylindrical lens 102 is set to be shorter than that of the cylindrical lens 101.

Arrows A and B of the cylindrical lenses 101 and 102 indicate a generatrix direction of each lens. In the present embodiment, both the generatrix directions are set to vertical directions perpendicular to the sliding direction of the sliding plate 105a, for example. Accordingly, even if either of the cylindrical lenses 101 and 102 is used, the change of the ellipse direction of the image of the sample 8 formed on the imaging device 14 is prevented. Alternatively, the cylindrical lenses 101 and 102 can be disposed such that both the generatrix directions become horizontal directions (sliding direction of the sliding plate 105a).

In such a configuration of the cylindrical lens unit 50, the control unit 25 drives the driving section 105b to slide the sliding plate 105a. Accordingly, the cylindrical lens unit 50 can perform switching between the cylindrical lenses 101 and 102 inserted into the optical path of the imaging optical system 7. In this manner, the microscope apparatus 100 can acquire an image of the sample 8 based on a three-dimensional method to be described later. In addition, the microscope apparatus 100 can acquire an image of the sample 8 based on a two-dimensional method since the opening section 106 can be inserted into the optical path within the imaging optical system 7 by driving the sliding plate 105a.

Figure 3:
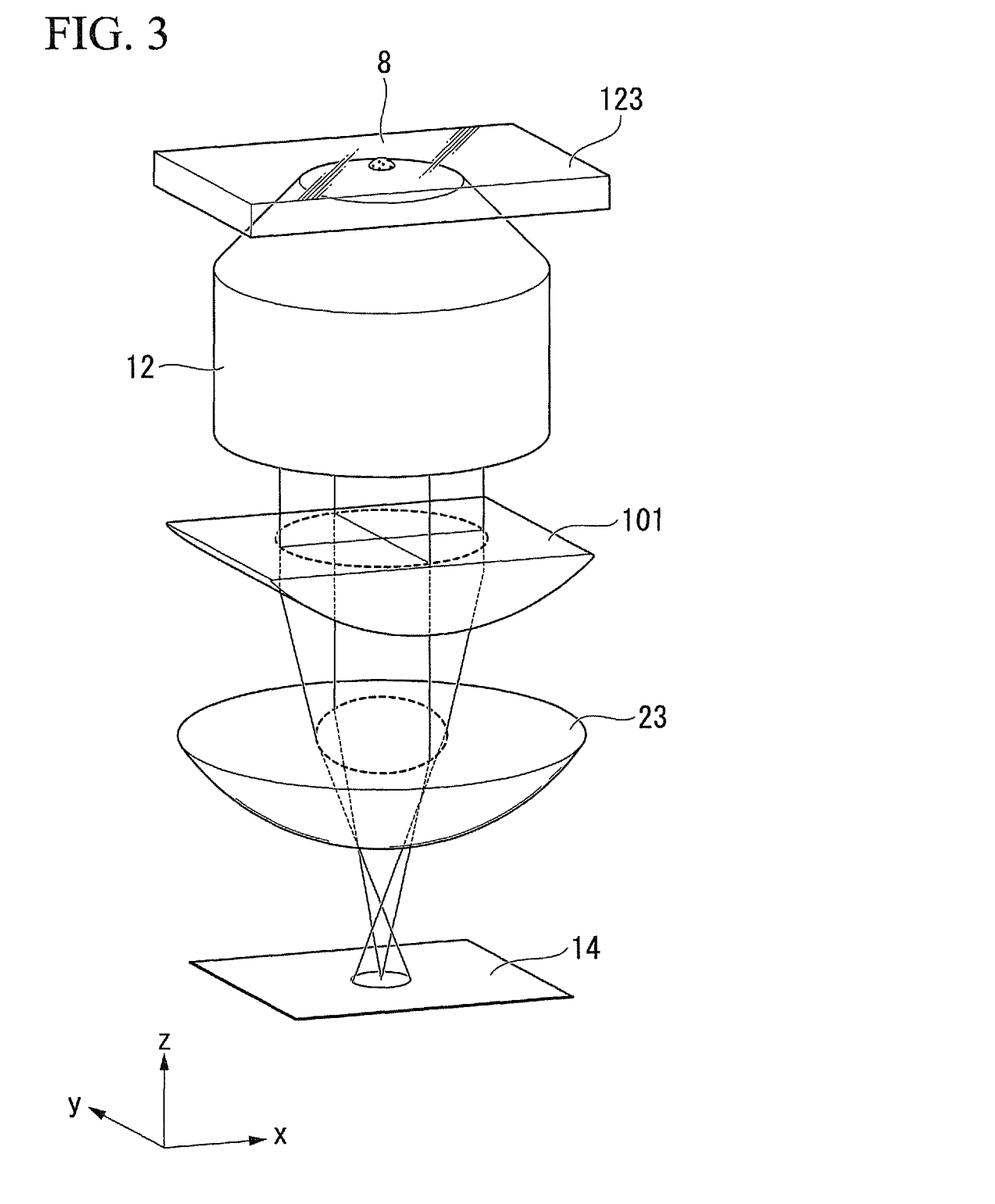
FIG. 3 is a view showing the schematic configuration of an imaging optical system of the microscope apparatus.

FIG. 3 is a schematic configuration diagram of the imaging optical system of the microscope apparatus 100 and specifically, shows a state where the cylindrical lens 101 is inserted into the optical path by the sliding plate 105a. In addition, for ease understanding, an illumination device 9, the imaging lens 20, the prism 21, and the lenses 22, and 23 are not shown in the drawing. In addition, an XYZ coordinate system is set in FIG. 3 for convenience of explanation, and explanation will be given using the XYZ coordinate system appropriately. In the XYZ coordinate system, the X and Y axes are set along the horizontal plane, and the Z axis is set along the vertical direction, for example. In addition, it is assumed that the XYZ coordinate system is effective in only FIG. 3.

Light beams from the sample 8 are incident on the objective lens 12 to become parallel light beams, and the parallel light beams are incident on the imaging lens 20. In the state shown in FIG. 3, a case will be described in which the cylindrical lens 101 is disposed between the imaging lens 20 and the imaging device 14. The cylindrical lens 101 is disposed such that the generatrix direction is the Y direction. The cylindrical lens 101 has refractive power in the X direction but does not have refractive power in the Y direction (generatrix direction).

Figure 4:
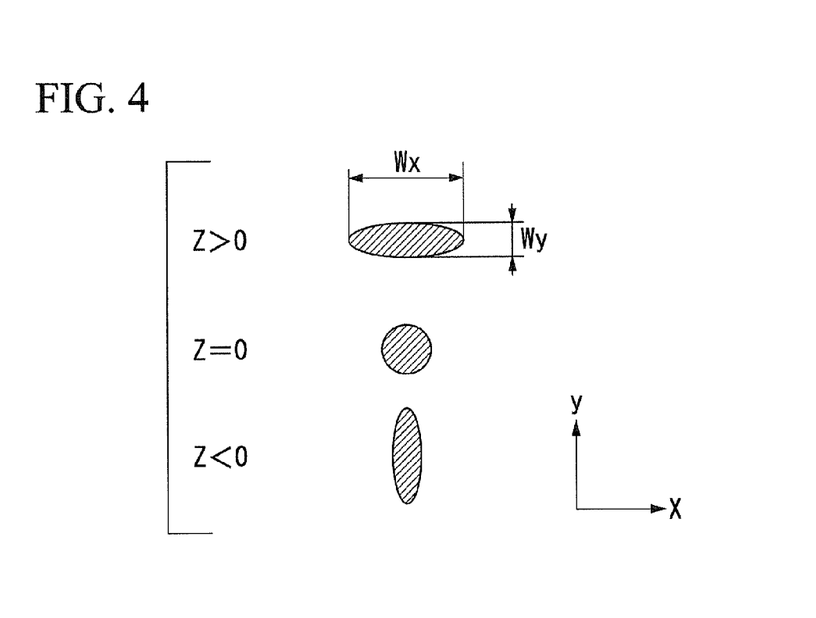
FIG. 4 is a view showing the shape of an image formed on an imaging device by one fluorescent material.

FIG. 4 is a view showing the shape of an image that is formed on the imaging device 14 by one fluorescent material present on the surface of the sample 8. Typically, a fluorescent material that is smaller than the resolution of the imaging optical system forms a circular image on the imaging device 14. In the present embodiment, since the imaging optical system 7 including the cylindrical lens 101 is used, the width (Wx) of an image in the X direction and the width (Wy) of the image in the Y direction change according to the Z coordinate. Assuming that the Z coordinate of a fluorescent material whose image is circular (Wx=Wy) is Z=0, the image becomes an ellipse (Wx>Wy) having a long axis in the X direction when Z>0 and an ellipse (Wx<Wy) having a long axis in the Y direction when Z<0. That is, in an image that is formed on the imaging device 14 by one fluorescent material given to the sample 8, the X-direction width and the Y-direction width change according to the Z coordinate, as will be described later.

Figure 5:
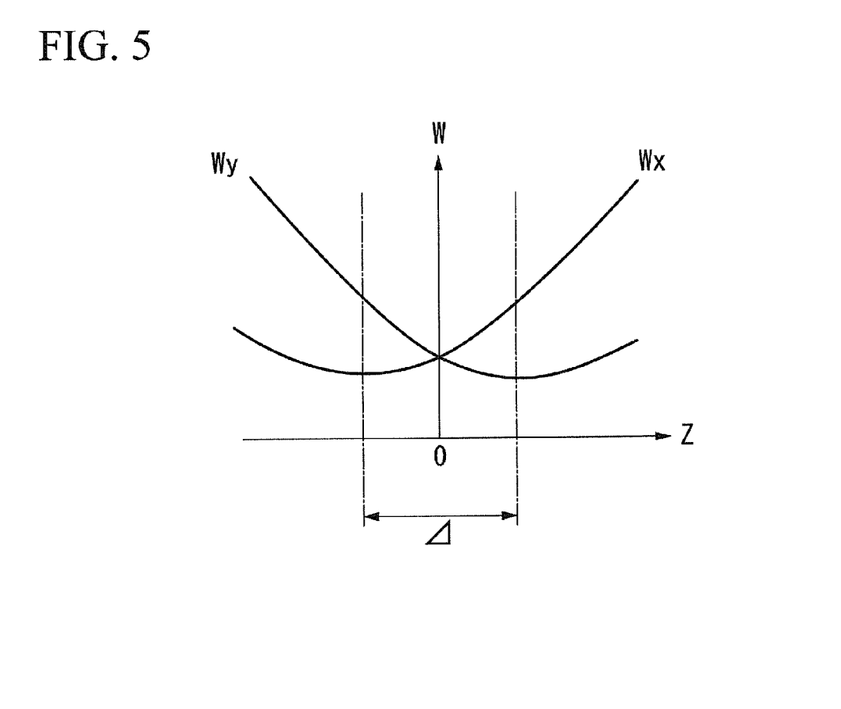
FIG. 5 is a graph showing the relationship between the Z coordinate of a fluorescent material and the width in each of the X and Y directions.

FIG. 5 is a graph showing the relationship between the Z coordinate (horizontal axis) of a fluorescent material and the width (vertical axis) in each of the X and Y directions. The widths Wx and Wy in the X and Y directions are minimum values in Z<0 and Z>0, respectively. In other words, Wx is a minimum at a certain Z position less than 0. Wy is a minimum at a certain Z position exceeding 0. At Z=0, Wx=Wy. The difference A between the Z coordinates at which Wx and Wy are minimums is an astigmatic difference. In other words, the astigmatic difference is a difference between the Z position at which Wx is a minimum and the Z position at which Wy is a minimum.

A method of observing an image of the sample 8 in the microscope apparatus 100 includes a step of emitting the low-power activation light L1 from the first laser light source 41a in the laser unit 40 to the sample 8, a step of acquiring a fluorescent image by emitting the high-power excitation light L2 from the second laser light source 9b to the sample 8 by switching of the shutters 42a and 42b and the acousto-optical element 45 in the laser unit 40, and a step of storing a fluorescent image measured as described above. This sample image observation method is performed by repeating these steps hundreds of times to tens of thousands of times.

The microscope apparatus 100 stores data, in which the Z coordinate is linked with the rate of change (the ratio of the width in the X direction and the width in the Y-direction; Wy/Wx) of an image when the cylindrical lens 101 is disposed between the imaging lens 3 and the imaging device 14 and which is calculated in advance by experiment or the like, in the control unit 25. In the microscope apparatus 100, it is possible to detect the Z coordinate of an image (fluorescent material) by comparing the data stored in the control unit 25 with data obtained by imaging the shape of an image that is formed on the imaging device 14 by each fluorescent material present on the surface of the sample 8. Thus, the microscope apparatus 100 captures an image to which an astigmatic difference is given using the imaging device 14, obtains the position (including the position in the Z direction) of a fluorescent material from each image, and disposes them in one image. Therefore, a high-resolution image of the sample 8 including the three-dimensional information (Z coordinate) can be acquired using the microscope apparatus 100.

Figure 6A:
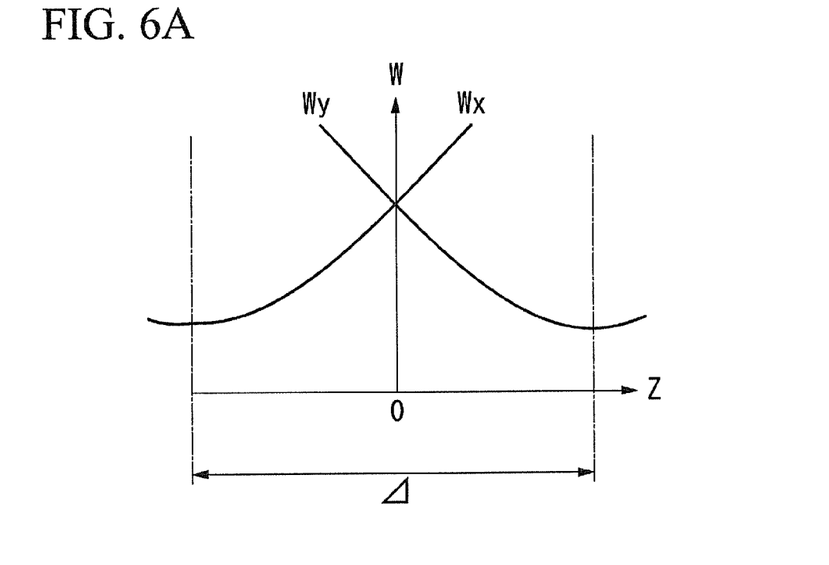
FIG. 6A is a view showing the relationship between the magnification of an objective lens, and the focal length and the astigmatic difference of a cylindrical lens.

Meanwhile, the above-described astigmatic difference should be adjusted so as to become a predetermined amount in accordance with the depth of focus of the objective lens. FIG. 6A is a graph showing the relationship between Z and Wx, Wy when the astigmatic difference is relatively large compared with the depth of focus of the objective lens.

As shown in FIG. 6A, when the astigmatic difference is relatively large compared with the depth of focus of the objective lens, Wx or Wy greatly increases even if Z shifts slightly from the position of Z=0. If the image becomes too large, the intensity on the imaging device 14 is reduced, and this reduces the S/N. As a result, since error in Wx and Wy obtained from the acquired image tends to increase, the Z coordinate of the image may not be able to be obtained correctly.

Figure 6B:
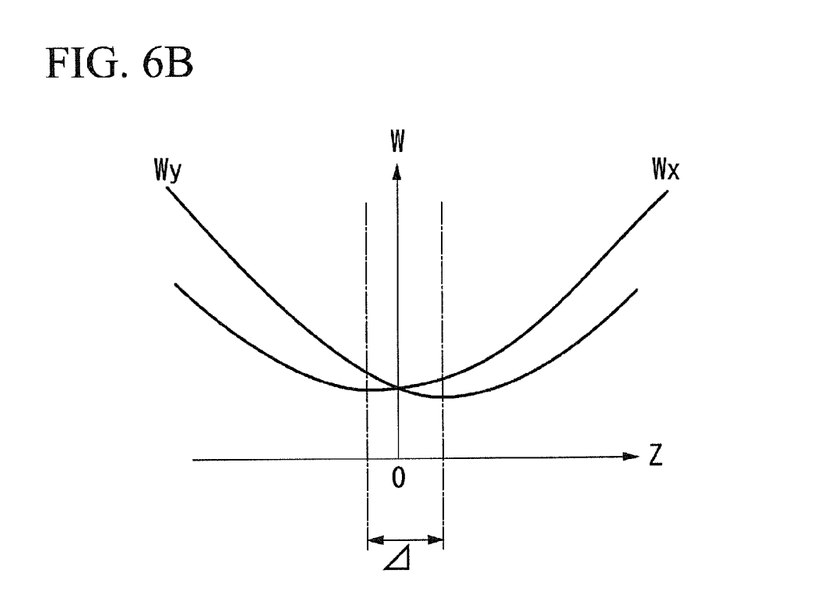
FIG. 6B is a view showing the relationship between the magnification of an objective lens, and the focal length and the astigmatic difference of a cylindrical lens.

On the other hand, FIG. 6B is a graph showing the relationship between Z and Wx, Wy when the astigmatic difference is relatively small compared with the depth of focus of the objective lens. As shown in FIG. 6B, when the astigmatic difference is relatively small compared with the depth of focus of the objective lens, the rate of change of ellipticity (Wy/Wx) in the vicinity of Z=0 is small. As a result, since slight error included in Wx and Wy obtained from the image tends to become large error in the Z coordinate calculation result, the Z coordinate of the image may not be able to be obtained correctly.

Therefore, when performing image observation based on the three-dimensional method, the astigmatic difference can be adjusted to fall within the optimal range by using a cylindrical lens having an appropriate focal length according to the depth of focus of the objective lens 12.

Specifically, it is preferable to set the astigmatic difference to twice the depth of focus of the objective lens. Assuming that the numerical aperture of the objective lens is NA, the refractive index of the medium in contact with the sample side surface of the objective lens is n, and the fluorescence wavelength of the dye is λ, the depth of focus FD is expressed by the following expression.

$$FD = (n\lambda)/(2NA^2) \quad (1)$$

On the other hand, assuming that the focal length of the cylindrical lens is f and the distance from the cylindrical lens to the image surface is d, an astigmatic difference Δ' on the image side caused by the cylindrical lens is expressed by the following expression.

$$\Delta' = (d^2)/(f+d) \quad (2)$$

In addition, assuming that the magnification of the objective lens is β, the value Δ which is a value of the astigmatic difference converted on the object side is expressed by the following expression.

$$\Delta = (n\Delta')/(\beta^2) \quad (3)$$

In order to set the astigmatic difference to twice the depth of focus, it is preferable to satisfy the following conditional expression.

$$\Delta = 2FD \quad (4)$$

If the expressions (1) to (4) are solved for f, the following expression is obtained.

$$f = (d^2 \cdot NA^2)/(\beta^2 \cdot \lambda) \quad (5)$$

Accordingly, if the focal length of the cylindrical lens is changed according to the used objective lens so that the expression (5) is satisfied, an appropriate astigmatic difference is obtained.

For example, when observing the fluorescence dye with a fluorescence wavelength of 550 nm using an objective lens with a magnification of 100 and a NA of 1.4, it is preferable to dispose a cylindrical lens with a focal length of 841 mm at the position of 50 mm from the image surface. In addition, when using an objective lens with a magnification of 60 and a NA of 1.4, it is preferable to change the focal length of the cylindrical lens to 2425 mm. In addition, when using an objective lens with a magnification of 20 and a NA of 0.75, it is preferable to change the focal length of the cylindrical lens to 6342 mm.

In the microscope apparatus 100 according to the present embodiment, the cylindrical lens unit 50 includes the cylindrical lens 101 corresponding to the objective lens 12a having a small depth of focus and the cylindrical lens 102 corresponding to the objective lens 12a having a large depth of focus. The focal length of the cylindrical lens 101 is different from the focal length of the cylindrical lens 102. That is, the microscope apparatus 100 is configured to include a plurality of cylindrical lenses 101 and 102 having different focal lengths and to select the cylindrical lens having an appropriate focal length according to the depth of focus of the used objective lens 12.

In the microscope apparatus 100, when image acquisition based on the three-dimensional method is performed using the low-magnification objective lens 12a, the control unit 25 drives the driving section 105b of the cylindrical lens unit 50 to slide the sliding plate 105a so that the cylindrical lens 101 is inserted into the optical path within the imaging optical system 7. On the other hand, in the microscope apparatus 100, when the high-magnification objective lens 12b is selected by the observer 38, the control unit 25 drives the driving section 105b of the cylindrical lens unit 50 to slide the sliding plate 105a so that the cylindrical lens 102 is inserted into the optical path of light from the imaging optical system 7.

As described above, in the microscope apparatus 100, the magnification and the numerical aperture of the objective lens 12 are changed according to the image acquisition conditions. In addition, in the microscope apparatus 100, even when the depth of focus is changed, either of the cylindrical lenses 101 and 102 having an optimal focal length corresponding to the objective lens 12 is selected. Accordingly, since an astigmatic difference in a predetermined range can be set, image observation of the sample 8 based on the three-dimensional method can be performed with high accuracy.

In addition, in the microscope apparatus 100, when the observer 38 desires image acquisition based on the two-dimensional method, the control unit 25 drives the driving section 105b of the cylindrical lens unit 50 to slide the sliding plate 105a so that the opening section 106 is inserted into the optical path of light from the imaging optical system 7. In this case, since the light from the sample 8 passes through the opening section 106, the image is not deformed into the elliptical shape unlike the case in which the light from the sample 8 passes through the cylindrical lens, and accordingly the image becomes a circular image on the imaging device 14. In this manner, in the microscope apparatus 100, a two-dimensional image of the sample 8 can be acquired based on the circular image captured by the imaging device 14.

In addition, although the case of two types of correspondence relationship between the cylindrical lenses 101 and 102 and the objective lens 12 has been described in the above embodiment, the present invention can also be applied to cases where three or more types of cylindrical lenses and an objective lens are combined. For example, the number of types of cylindrical lenses can be set to 2, 3, 4, 5, 6, 7, 8, 9, 10, or more. In this case, each cylindrical lens has a focal length, by which the optimal astigmatic difference can be set, when combined with the linked objective lens 12.

(Second Embodiment)

Next, a second embodiment of the microscope apparatus of the present invention will be described. In addition, the only difference between the configuration according to the present embodiment and the configuration according to the first embodiment is the configuration of the objective lens unit and the cylindrical lens unit. For this reason, in the following explanation, the configuration of the cylindrical lens unit will mainly be described. In addition, the same configurations and members as in the first embodiment are denoted by the same reference numerals, and detailed explanation thereof will be omitted or simplified.

Figure 7:
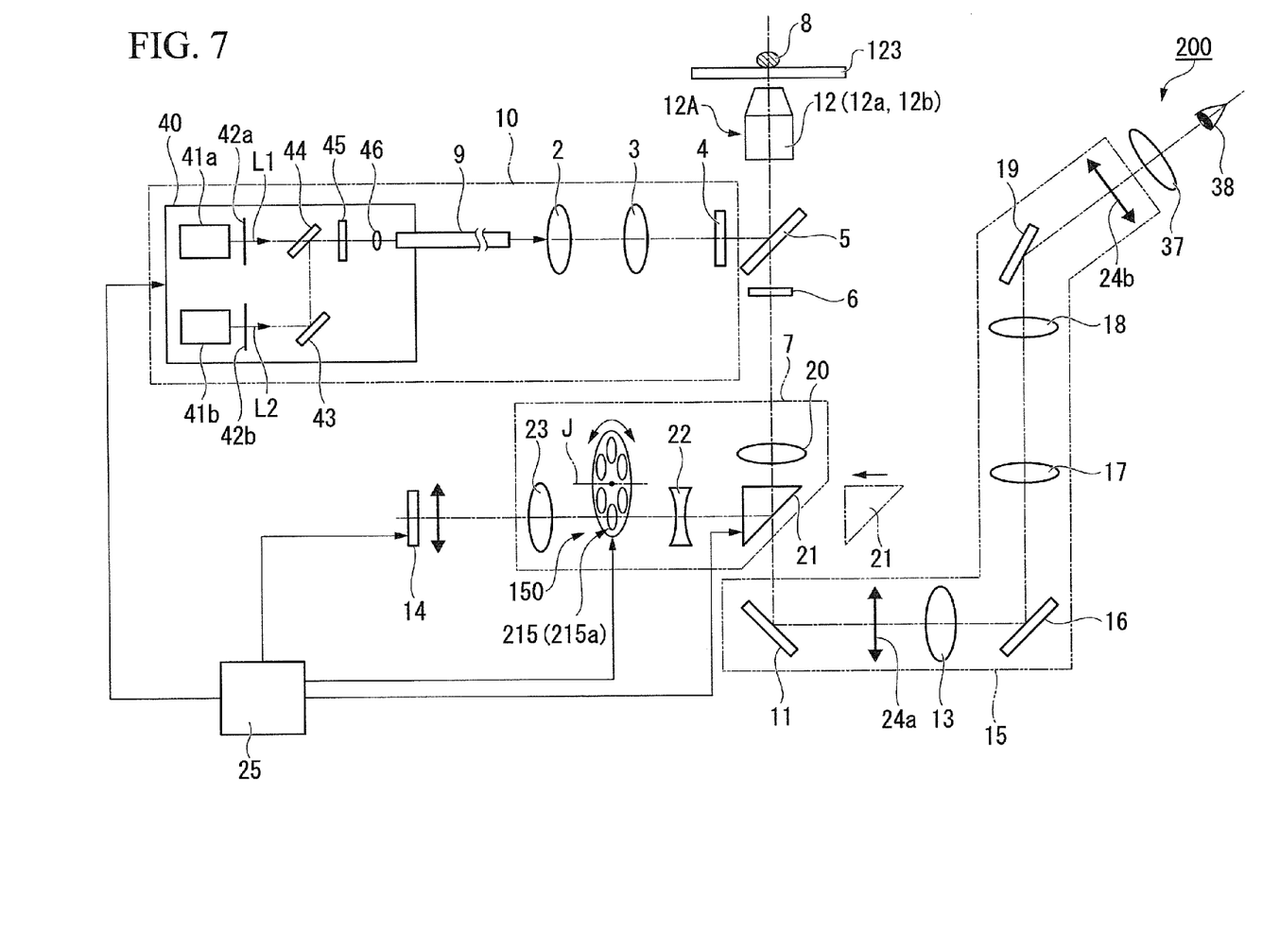
FIG. 7 is a view showing the schematic configuration of a microscope apparatus according to a second embodiment.
Figure 8:
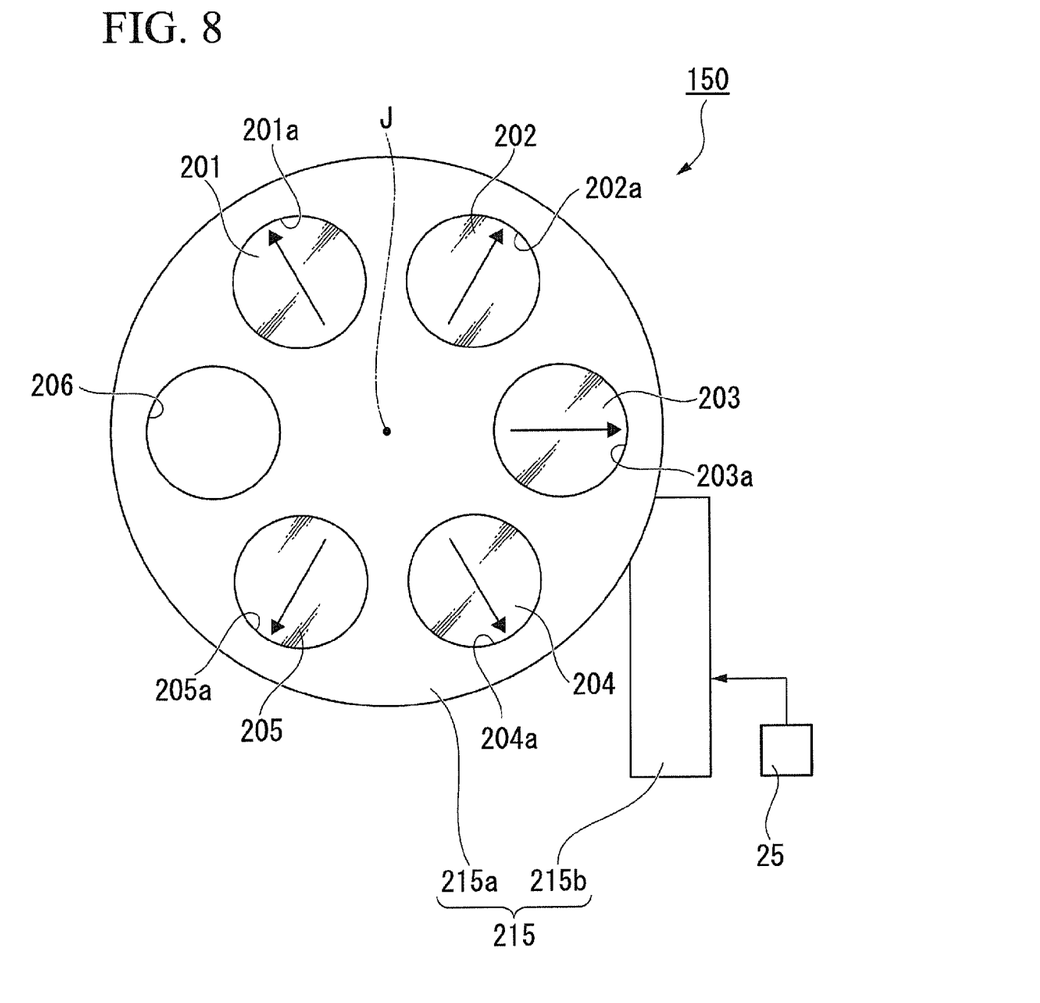
FIG. 8 is a view showing the configuration of a cylindrical lens unit according to the present embodiment.

FIG. 7 is a view showing the schematic configuration of a microscope apparatus according to the present embodiment, and FIG. 8 is a view showing the configuration of a cylindrical lens unit in the present embodiment.

In the present embodiment, as shown in FIG. 7, an objective lens unit 112A includes a first objective lens 112a, a second objective lens 112b, a third objective lens 112c, a fourth objective lens 112d, and a fifth objective lens 112e. The depth of focus of each of the first to fifth objective lenses 112a to 112e is set so as to increase in this order. That is, the depth of focus of the first objective lens 112a is set to be smallest, and the depth of focus of the objective lens 112e is set to be largest. Hereinafter, for convenience of explanation, the first to fifth objective lenses 112a to 112e may be called collectively an objective lens 112.

In a microscope apparatus 200 according to the present embodiment, as shown in FIG. 7, a cylindrical lens unit 150 is provided between the lenses 22 and 23 in the imaging optical system 7. As shown in FIGS. 7 and 8, the cylindrical lens unit 150 includes a plurality of cylindrical lenses 201 to 205 and a turret section (reciprocating section) 215 that moves the cylindrical lenses 201 to 205 back and forth between the lenses 22 and 23. The turret section 215 includes a disk member 215a, which holds the cylindrical lenses 201 to 205, and a rotation driving section 215b, which can move each of the cylindrical lenses 201 to 205 back and forth between the lenses 22 and 23 by rotating it around the rotation axis J passing through the center of the disk member 215a.

Holding sections 201a to 205a of the cylindrical lenses 201 to 205 and an opening section 206 are provided in the disk member 215a. The holding sections 201a to 205a and the opening section 206 are disposed along the circumferential direction (rotation direction) of the disk member 215a. The opening section 206 is set to have a size allowing light transmitted through the lens 22 to pass therethrough without blocking the light. The cylindrical lenses 201 to 205 are held on the disk member 215a when fitted in the holding sections 201a to 205a, for example.

Each arrow in the cylindrical lenses 201 to 205 indicates a generatrix direction of each lens. In the present embodiment, each lens is attached such that each arrow is positioned toward the radial direction of the disk member 215a, for example. That is, the generatrix direction of each lens is set in a radial direction with respect to the center of the disk member 215a through which the rotation axis J passes, and the cylindrical lenses 201 to 205 are disposed such that the generatrix direction of each lens is a vertical direction when the cylindrical lenses 201 to 205 are inserted between the lenses 22 and 23. Accordingly, whichever of the cylindrical lenses 201 to 205 is used, the change of the ellipse direction of the sample 8 formed on the imaging device 14 is prevented. In addition, the cylindrical lenses 201 to 205 may be disposed such that each generatrix direction is a circumferential direction (direction perpendicular to the radial direction). The cylindrical lenses 201 to 205 have different focal lengths. Specifically, the focal lengths of the cylindrical lenses 201 to 205 are set so as to decrease in order of the cylindrical lens 205 to the cylindrical lens 201. That is, the focal length of the cylindrical lens 205 is largest, and the focal length of the cylindrical lens 201 is smallest.

In the present embodiment, the first objective lens 112a having a smallest depth of focus among the objective lenses 112 is linked with the cylindrical lens 205 having a largest focal length in the cylindrical lens unit 150. On the other hand, the fifth objective lens 112e having a largest depth of focus is linked with the cylindrical lens 201 having a smallest focal length in the cylindrical lens unit 150. In addition, the second objective lens 112b is linked with the cylindrical lens 204, the third objective lens 112c is linked with the third cylindrical lens 203, and the fourth objective lens 112d is linked with the fourth cylindrical lens 202.

Based on such a configuration, according to the type of the objective lens 112 selected by the observer 38, the control unit 25 in the microscope apparatus 200 drives the rotation driving section 215b of the cylindrical lens unit 150 to rotate the disk member 215a so that the corresponding cylindrical lenses 201 to 205 are inserted into the optical path of the imaging optical system 7. Therefore, in the microscope apparatus 200, even if the magnification and the numerical aperture of the objective lens 112 are changed according to the image acquisition conditions that the observer 38 desires, the optimal cylindrical lenses 201 to 205 corresponding to the objective lens 112 can be set. As a result, image observation of the sample 8 based on the three-dimensional method can be performed with high accuracy.

In addition, in the microscope apparatus 200, when the observer 38 desires image acquisition based on the two-dimensional method, the control unit 25 drives the rotation driving section 215b of the cylindrical lens unit 150 to rotate the disk member 215a so that the opening section 206 is inserted into the optical path of the imaging optical system 7. In this case, since the light from the sample 8 passes through the opening section 206, the image is not deformed into the elliptical shape unlike the case in which the light from the sample 8 passes through the cylindrical lenses 201 to 205, and accordingly, the image becomes a circular image on the imaging device 14. In this manner, in the microscope apparatus 200, a two-dimensional image of the sample 8 can be acquired using a two-dimensional method based on the circular image captured by the imaging device 14.

In addition, although the case of five types of correspondence relationship between the cylindrical lenses 201 to 205 and the objective lens 112 has been described in the above embodiment, the present invention can also be applied to cases fewer than five types or cases of six or more types. For example, the number of correspondence relationships between the cylindrical lenses 201 to 205 and the objective lens 112 can be set to 2, 3, 4, 5, 6, 7, 8, 9, 10, or more.

(Third Embodiment)

Next, a third embodiment of the microscope apparatus of the present invention will be described. In addition, the only difference between the configuration according to the present embodiment and the configuration according to the first and second embodiments is the configuration of the cylindrical lens unit. For this reason, in the following explanation, the configuration of the cylindrical lens unit will mainly be described. In addition, the same configurations and members as in the embodiments described above are denoted by the same reference numerals, and detailed explanation thereof will be omitted or simplified.

Figure 9:
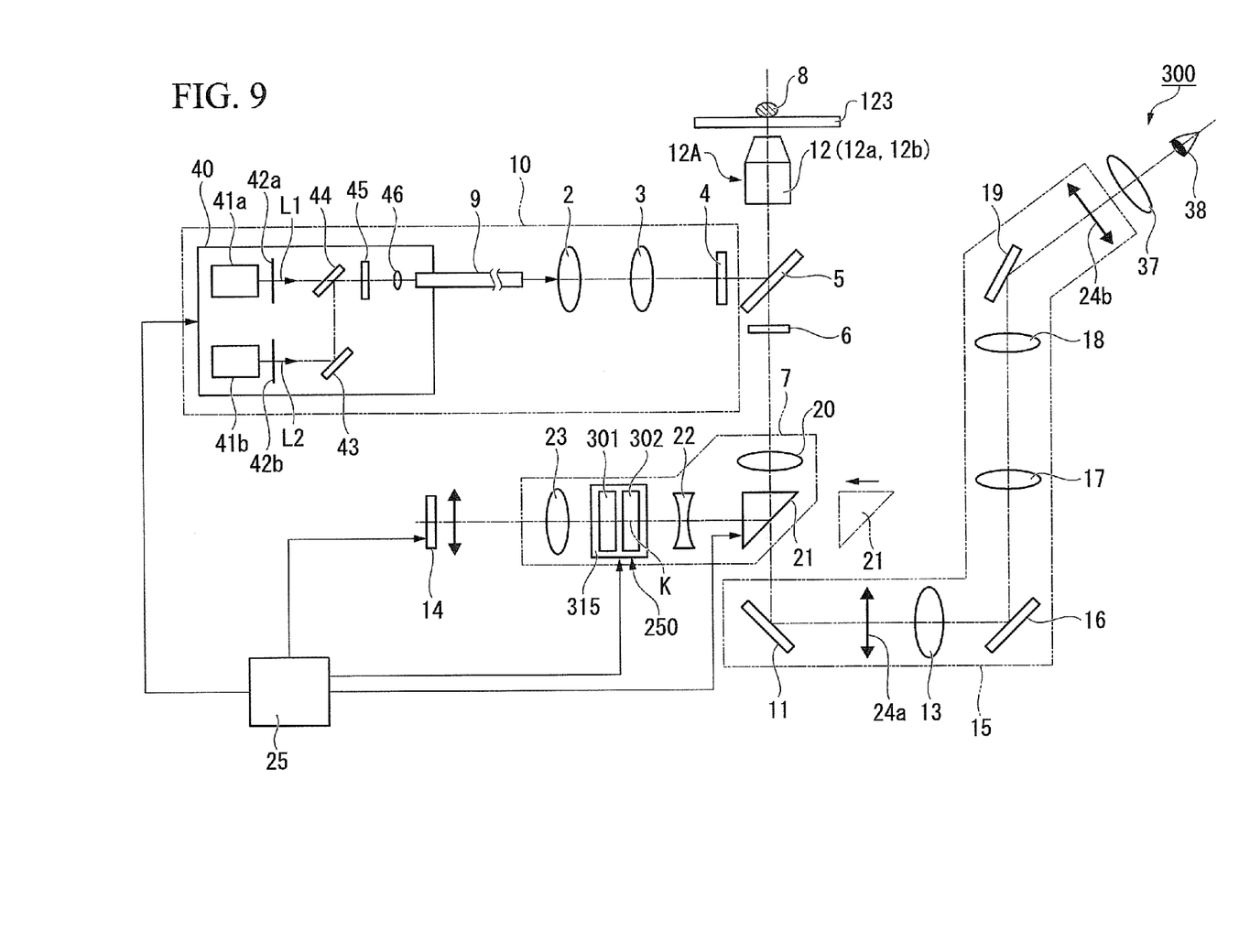
FIG. 9 is a view showing the schematic configuration of a microscope apparatus according to a third embodiment.
Figure 10:
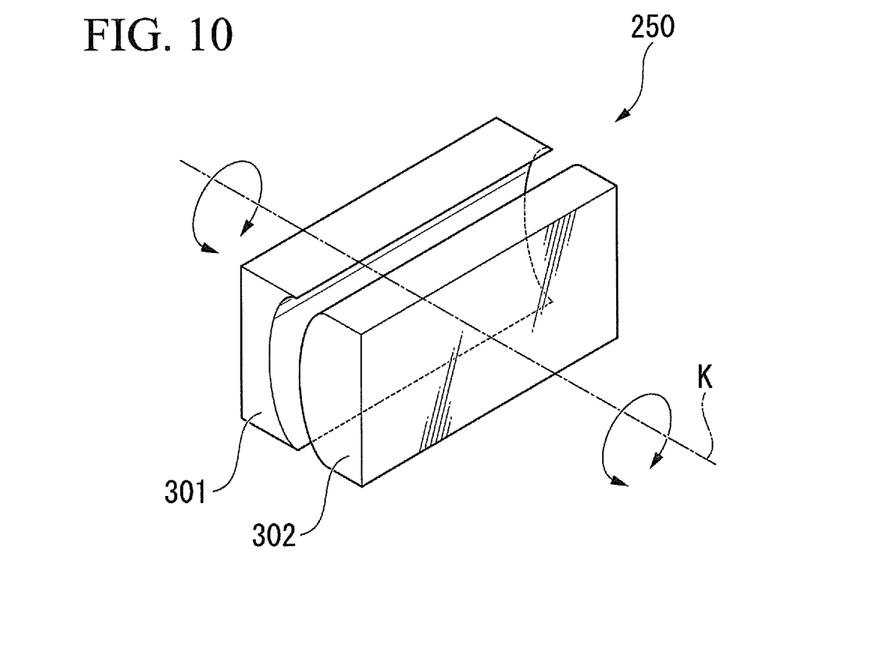
FIG. 10 is a view showing the configuration of a cylindrical lens unit according to the present embodiment.

FIG. 9 is a view showing the schematic configuration of a microscope apparatus 300 according to the present embodiment, and FIG. 10 is a view showing the configuration of a cylindrical lens unit in the present embodiment.

In the microscope apparatus 300 according to the present embodiment, as shown in FIG. 9, a cylindrical lens unit 250 is provided between the lenses 22 and 23 in the imaging optical system 7. The cylindrical lens unit 250 according to the present embodiment includes a pair of cylindrical lenses 301 and 302 and a rotating cylinder section 315 that holds the cylindrical lenses 301 and 302. The rotating cylinder section 315 holds the pair of cylindrical lenses 301 and 302 in a state where each of the pair of cylindrical lenses 301 and 302 can rotate around a predetermined rotation axis K. Here, the predetermined rotation axis K in the cylindrical lens 301 and 302 is defined by the axis parallel to the central axis of light beams of an image within the imaging optical system 7. It is possible to change the astigmatic difference continuously since the cylindrical lenses 301 and 302 rotate with respect to each other.

The cylindrical lenses 301 and 302 have different positive and negative focal lengths whose absolute values are equal. Specifically, in the present embodiment, as shown in FIG. 10, a concave cylindrical lens has been used as the cylindrical lens 301 and a convex cylindrical lens has been used as the cylindrical lens 302.

Figure 11:
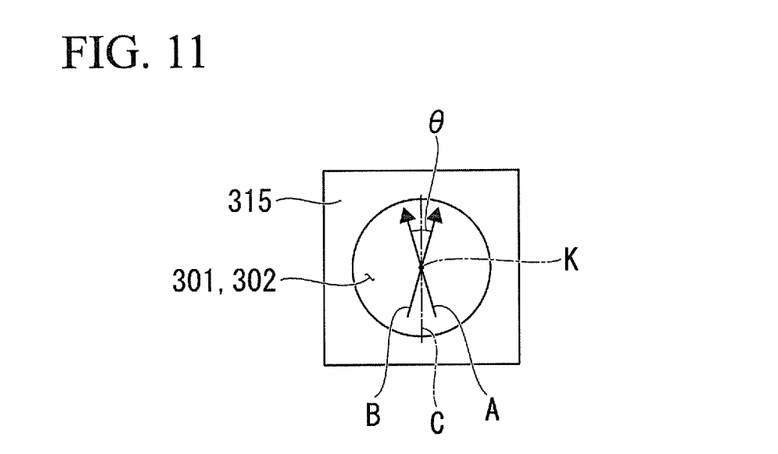
FIG. 11 is a view when the cylindrical lens unit is viewed from the rotation axis direction.
Figure 12A:
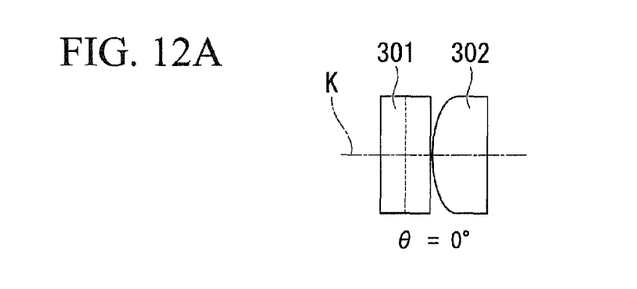
FIG. 12A is a view showing the positional relationship between cylindrical lenses.
Figure 12B:
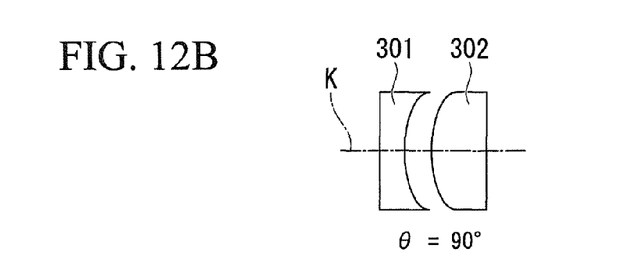
FIG. 12B is a view showing the positional relationship between cylindrical lenses.

FIG. 11 is a view when the cylindrical lens unit 250 is viewed from the axial direction of the rotation axis K. The arrow A in FIG. 11 indicates a generatrix direction of the cylindrical lens 301 and the arrow B in FIG. 11 indicates a direction of curvature (direction perpendicular to the generatrix direction) of the cylindrical lens 302, and the angle formed by the arrows A and B is set to 8. In addition, in FIG. 11, for easy understanding of explanation, the shape of each of the cylindrical lenses 301 and 302 is simplified and shown as a circular shape. FIG. 12A is a plan view showing a state of the cylindrical lenses 301 and 302 when the angle θ formed by the arrows A and B is 0°, and FIG. 12B is a plan view showing a state of the cylindrical lenses 301 and 302 when the angle θ formed by the arrows A and B is 90°.

The cylindrical lenses 301 and 302 rotate with respect to each other so that θ changes while always maintaining the median line C (combined generatrix) of the two arrows A and B in the vertical direction. That is, the cylindrical lenses 301 and 302 are configured to rotate by the same angle in the opposite directions, and the angle formed by each of the arrows A and B and the median line C is θ/2. Thus, since the cylindrical lens unit 250 always maintains the median line C of the arrows A and B in the vertical direction, the rotation of the ellipse direction of the image of the sample 8 formed on the imaging device 14 is prevented.

In the cylindrical lens unit 250, as shown in FIG. 12A, when θ is 0°, the astigmatic difference is largest since the difference in the refractive power of the lens in the vertical direction and the horizontal direction is maximized. On the other hand, as shown in FIG. 12B, when θ is 90°, the astigmatic difference is θ since there is no difference in the refractive power of the lens in the vertical direction and the horizontal direction. Thus, the cylindrical lens unit 250 can change the astigmatic difference continuously by adjusting θ between 0° and 90°. In addition, the microscope apparatus 300 stores data, which is obtained in advance by experiment or the like and in which the depth of focus of the objective lens 112 is linked with the rotation angle θ of the lenses 301 and 302 to generate the astigmatic difference corresponding to the depth of focus, in the control unit 25.

In the microscope apparatus 300, according to the type of the objective lens 112 selected by the observer 38, the control unit 25 drives the rotating cylinder section 315 of the cylindrical lens unit 250 to rotate a pair of cylindrical lenses 301 and 302 by a predetermined angle. Therefore, in the microscope apparatus 300, even if the magnification and the numerical aperture of the objective lens 112 are changed according to the image acquisition conditions that the observer 38 desires, the optimal astigmatic difference corresponding to the depth of focus of the objective lens 112 can be set. As a result, it is possible to provide image observation of the sample 8 based on the high-accuracy three-dimensional method.

In addition, in the microscope apparatus 300, when the observer 38 desires image acquisition based on the two-dimensional method, the control unit 25 drives the rotating cylinder section 315 of the cylindrical lens unit 250 to set the angle θ of a pair of cylindrical lenses 301 and 302 to 90°. In this case, since light from the sample 8 does not cause an astigmatic difference when the light passes through the cylindrical lenses 301 and 302, the image is not deformed, and accordingly the image becomes a circular image on the imaging device 14. In this manner, in the microscope apparatus 300, an image of the sample 8 can be acquired using a two-dimensional method based on the circular image captured by the imaging device 14.

(Fourth Embodiment)

Next, a fourth embodiment of the microscope apparatus of the present invention will be described. In addition, the only difference between the configuration according to the present embodiment and the configuration according to the second and third embodiments is the configuration of the cylindrical lens unit. For this reason, in the following explanation, the configuration of the cylindrical lens unit will mainly be described. In addition, the same configurations and members as in the first embodiment are denoted by the same reference numerals, and detailed explanation thereof will be omitted or simplified.

Figure 13:
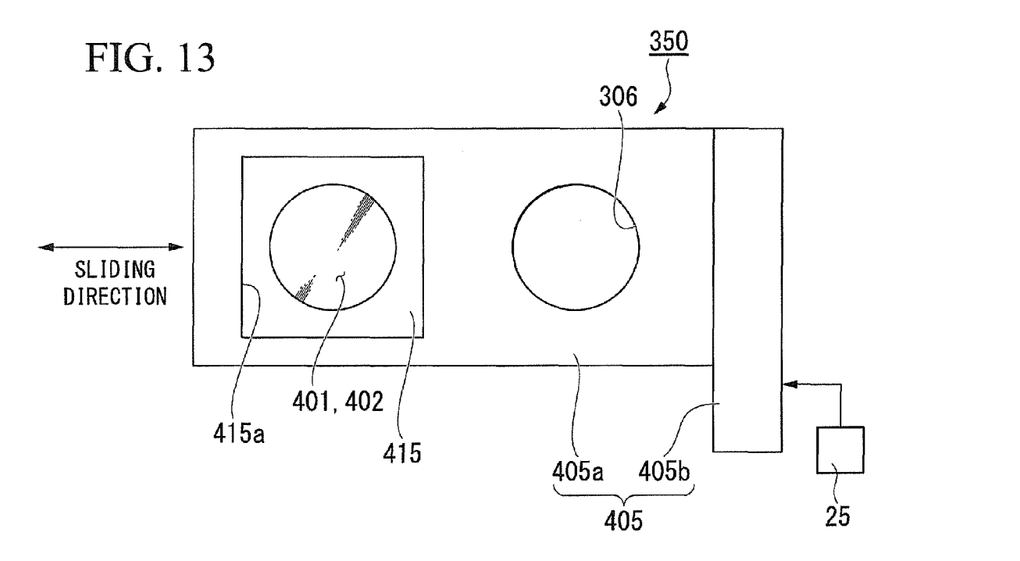
FIG. 13 is a view showing the schematic configuration of a cylindrical lens unit according to a fourth embodiment.

FIG. 13 is a view showing the configuration of a cylindrical lens unit according to the present embodiment. The cylindrical lens unit according to the present embodiment is obtained by combining part of the configuration of the cylindrical lens unit of the first embodiment and part of the configuration of the cylindrical lens unit of the third embodiment.

Specifically, as shown in FIG. 13, a cylindrical lens unit 350 according to the present embodiment includes a rotating cylinder section 415, which holds a pair of cylindrical lenses 401 and 402, and a slider section (reciprocating section) 405. The slider section 405 includes a sliding plate 405a that holds the rotating cylinder section 415 slidably and a driving section 405b that slides the sliding plate 405a.

A holding section 415a of the rotating cylinder section 415 and an opening section 306 are provided in the sliding plate 405a. The holding section 315a and the opening section 306 are disposed along the sliding direction (horizontal direction) of the sliding plate 405a. The opening section 306 is set to have a size allowing light transmitted through the lens 22 to pass therethrough without blocking the light. The rotating cylinder section 415 is held on the sliding plate 405a when fitted in the holding section 415a.

In the present embodiment, convex cylindrical lenses have been used as both the cylindrical lenses 401 and 402. For this reason, although the astigmatic difference cannot be set to 0 unlike the third embodiment in which the convex cylindrical lens and the concave cylindrical lens are combined, a state where the astigmatic difference is 0 (image observation based on the two-dimensional method) is possible by combining the above-described opening section 306 in the present embodiment.

In the microscope apparatus according to the present embodiment, when performing image acquisition based on the three-dimensional method, the control unit 25 drives a driving section 405b of the cylindrical lens unit 350 to slide the sliding plate 405a so that the rotating cylinder section 415 is inserted into the optical path within the imaging optical system 7. In this case, according to the type of the objective lens 112 selected by the observer 38, the control unit 25 drives the rotating cylinder section 415 to rotate a pair of cylindrical lenses 401 and 402 by a predetermined angle. Therefore, in the microscope apparatus, even if the magnification and the numerical aperture of the objective lens are changed according to the image acquisition conditions that the observer 38 desires, the optimal astigmatic difference corresponding to the depth of focus of the objective lens can be set. As a result, image observation of the sample 8 based on the three-dimensional method can be performed with high accuracy.

In addition, in the microscope apparatus according to the present embodiment, when the observer 38 desires image acquisition based on the two-dimensional method, the control unit 25 drives the driving section 405b of the cylindrical lens unit 350 to slide the sliding plate 405a so that the opening section 306 is inserted into the optical path of light from the imaging optical system 7. In this case, since the light from the sample 8 passes through the opening section 306, the image is not deformed into the elliptical shape unlike the case in which the light from the sample 8 passes through the cylindrical lens, and accordingly the image becomes a circular image on the imaging device 14. In this manner, in the microscope apparatus, an image of the sample 8 can be acquired using a two-dimensional method based on the circular image captured by the imaging device 14.

In addition, it is also possible to adopt a configuration that changes a rotating cylinder and an opening section using the turret section according to the second embodiment. In addition, although the combination of a convex cylindrical lens and a convex cylindrical lens has been used as a pair of cylindrical lenses 401 and 402 in the fourth embodiment, it is also possible to use a combination of a concave cylindrical lens and a concave cylindrical lens.

In the above embodiments, the microscope apparatus using two lasers having different wavelengths for activation and excitation has been described. On the other hand, dSTORM (direct Stochastic Optical Reconstruction Microscopy) is known regarding a microscope using only the laser for excitation. In dSTORM, an image of only a small number of fluorescence dyes is acquired based on spontaneous blinking of a fluorescent material without laser irradiation for activation unlike the conventional STORM. The astigmatic difference changing device of the present invention can also be applied to the dSTORM.

In an embodiment, a microscope apparatus includes: a plurality of objective lenses having different magnifications; an imaging system that receives light, which is generated from a sample and emitted from the objective lenses when excitation light having a predetermined wavelength is emitted to the sample including a fluorescent material that fluoresces when irradiated with the excitation light, and that images the light in a state where the astigmatic difference is given to an image of the sample; and an imaging device that captures the image of the sample from the imaging system. The imaging system includes an astigmatic difference changing device that changes the astigmatic difference according to the depth of focus of the objective lens.

In an embodiment, a microscope apparatus includes: a plurality of objective lenses having different magnifications; an imaging system that receives light, which is generated from a sample and emitted from the objective lenses when excitation light is emitted to the sample including a fluorescent material that is activated when irradiated with activation light having a predetermined wavelength and fluoresces to be inactivated when irradiated with the excitation light having a different wavelength from the activation light in the activation state and that images the light in a state where an astigmatic difference is given to an image of the sample; and an imaging device that captures the image of the sample from the imaging system. The imaging system includes an astigmatic difference changing device that changes the astigmatic difference according to the depth of focus of the objective lens.

What is claimed is:

1. A microscope apparatus comprising:
an illumination optical system that is configured to irradiate a sample including a plurality of fluorescent materials with activation light and excitation light so as to activate and excite a portion of the plurality of fluorescent materials;
an imaging optical system that is configured to receive fluorescence, which is emitted from a portion of the plurality of fluorescent materials, through an objective lens and to form an image to which an astigmatic difference is given;
an imaging device that is configured to capture the image to which the astigmatic difference is given;
a control unit that is configured to control the illumination optical system to irradiate the sample with the activation light and the excitation light repeatedly, and to determine a three-dimensional position which is x-, y-, and z-positions of the plurality of fluorescent materials on the basis of a plurality of images which are obtained by capturing images to each of which the astigmatic difference is given, and
an astigmatic difference changing device so as to change the astigmatic difference,
wherein a plurality of objective lenses of which magnification is different from each other are switchably arranged in the imaging optical system, and
when one objective lens is switched by another objective lens, the control unit controls the astigmatic difference changing device to change the astigmatic difference according to a depth of focus of the another objective lens.

2. The microscope apparatus according to claim 1,
wherein the astigmatic difference changing device includes a plurality of cylindrical lenses capable of giving different astigmatic differences to the image of the sample and a reciprocating section that moves the plurality of cylindrical lenses back and forth with respect to an optical path of light emitted from the objective lens.

3. The microscope apparatus according to claim 2,
wherein the reciprocating section includes a disk member that is rotatable in a circumferential direction, and
the plurality of cylindrical lenses are disposed along the circumferential direction of the disk member.

4. The microscope apparatus according to claim 3,
wherein a generatrix direction of each of the plurality of cylindrical lenses is disposed toward a radial direction of the disk member.

5. The microscope apparatus according to claim 2,
wherein the reciprocating section includes a sliding plate that slides with respect to the optical path of the light emitted from the objective lens, and
the plurality of cylindrical lenses are disposed along a sliding direction of the sliding plate.

6. The microscope apparatus according to claim 5,
wherein a generatrix direction of each of the plurality of cylindrical lenses is disposed in a direction perpendicular to the sliding direction.

7. The microscope apparatus according to claim 2,
wherein the reciprocating section has an opening section for a two-dimensional image which is acquired without giving the astigmatic difference to the image of the sample.

8. The microscope apparatus according to claim 1,
wherein the imaging system includes an afocal optical system, and
the astigmatic difference changing device is disposed in the afocal optical system.

9. The microscope apparatus according to claim 1,
wherein the astigmatic difference is substantially twice as large as a depth of focus of the objective lens.

10. The microscope apparatus according to claim 1,
wherein the astigmatic difference changing device includes a pair of cylindrical lenses, and
the cylindrical lenses are rotatable with respect to each other around a predetermined rotation axis.

11. The microscope apparatus according to claim 10,
wherein the pair of cylindrical lenses rotate by the same angle in the opposite directions.

12. The microscope apparatus according to claim 11,
wherein a control unit that rotates the pair of cylindrical lenses controls the pair of cylindrical lenses based on data in which a depth of focus of the objective lens is linked with the angle.

13. The microscope apparatus according to claim 7,
wherein the astigmatic difference is substantially twice as large as a depth of focus of the objective lens.

* * * * *